United States Patent
Perry

(10) Patent No.: US 11,017,337 B2
(45) Date of Patent: May 25, 2021

(54) COMPUTERIZED DATA PROCESSING SYSTEMS AND METHODS FOR GENERATING INTERACTIVE GRAPHICAL USER INTERFACES

(71) Applicant: TeleTracking Technologies, Inc., Pittsburgh, PA (US)

(72) Inventor: Thomas Perry, Dubois, PA (US)

(73) Assignee: TeleTracking Technologies, Inc., Pittsburgh, PA (US)

( * ) Notice: Subject to any disclaimer, the term of this patent is extended or adjusted under 35 U.S.C. 154(b) by 712 days.

(21) Appl. No.: 15/390,073

(22) Filed: Dec. 23, 2016

(65) Prior Publication Data

US 2017/0185930 A1 Jun. 29, 2017

Related U.S. Application Data

(60) Provisional application No. 62/387,161, filed on Dec. 23, 2015.

(51) Int. Cl.
*G06Q 10/06* (2012.01)
*H04W 4/80* (2018.01)
(Continued)

(52) U.S. Cl.
CPC . *G06Q 10/06312* (2013.01); *G06Q 10/06315* (2013.01); *G06Q 10/063118* (2013.01);
(Continued)

(58) Field of Classification Search
CPC ..... G06Q 10/06312; G06Q 10/063118; G06Q 10/06315; G16H 40/20; G16H 40/63; H04W 4/80; H04L 67/26; H04L 67/42
(Continued)

(56) References Cited

U.S. PATENT DOCUMENTS 8,239,249 B1 * 8/2012 Belko .............. G06Q 10/06311
705/7.14
2007/0067199 A1 * 3/2007 Shine .................... G06Q 10/06
705/7.14

(Continued)

OTHER PUBLICATIONS

Barlow, Next-generation Tracking: Go Beyond Tracking People Products and Equipment, 10 Health Management Technology 35 (Oct. 23, 2014) (Year: 2014).*

(Continued)

*Primary Examiner* — Charles Guiliano
(74) *Attorney, Agent, or Firm* — Ference & Associates LLC

(57) ABSTRACT

Centralized communication server systems and methods are provided. In one embodiment, a centralized server includes at least one network interface for bidirectional communication with mobile devices. At least one processor is configured to receive, via the computer network, event information for a discharge event associated with an individual, automatically identify a department associated with the one or more rooms, automatically receive protocol information for the identified department, and identify one or more milestones. The processor(s) are further configured to automatically generate workload data based on the identified milestones, receive assignment information for a plurality of individuals associated with the protocol information, and automatically assign the one or more milestones to the first individual. The processor(s) are further configured to automatically generate a first electronic notification addressed to the first mobile device, including information associated with the at least one discharge event and the one or more milestones.

20 Claims, 7 Drawing Sheets

(51) Int. Cl.
  *G16H 40/20* (2018.01)
  *G16H 40/63* (2018.01)
  *H04L 29/08* (2006.01)
  *H04L 29/06* (2006.01)
(52) U.S. Cl.
  CPC ............. *G16H 40/20* (2018.01); *G16H 40/63* (2018.01); *H04L 67/26* (2013.01); *H04W 4/80* (2018.02); *H04L 67/42* (2013.01)
(58) Field of Classification Search
  USPC ...................................................... 705/7.13
  See application file for complete search history.

(56) References Cited

U.S. PATENT DOCUMENTS

| | | | | |
|---|---|---|---|---|
| 2008/0015903 | A1* | 1/2008 | Rodgers | G06Q 30/02 705/3 |
| 2008/0164998 | A1* | 7/2008 | Scherpbier | G16H 40/20 340/539.13 |
| 2009/0313046 | A1* | 12/2009 | Badgett | G06Q 10/06 705/3 |
| 2013/0204633 | A1* | 8/2013 | Jourdan | G06Q 10/06311 705/2 |
| 2013/0290213 | A1 | 10/2013 | Deasaro | |
| 2013/0325508 | A1* | 12/2013 | Johnson | G06F 19/3418 705/3 |
| 2015/0109442 | A1* | 4/2015 | Derenne | A61B 5/1113 348/143 |
| 2016/0000951 | A1* | 1/2016 | Kreiner | A61L 2/10 422/24 |

OTHER PUBLICATIONS

Extended European Search Report for corresponding European Application No. 16206885.2 dated Mar. 10, 2017 (8 pages).

* cited by examiner

COMPUTERIZED DATA PROCESSING SYSTEMS AND METHODS FOR GENERATING INTERACTIVE GRAPHICAL USER INTERFACES

PRIORITY CLAIM

This application claims priority from U.S. Provisional Application No. 62/387,161, filed Dec. 23, 2015, which is hereby incorporated by reference in its entirety in the present application.

TECHNICAL FIELD

The present disclosure is directed to the technical field of centralized event detection and communications. More particularly, disclosed embodiments are directed to centralized server-based communication systems for generating automated electronic messages in a facility based on detected events. The data processing system may automate one or more processes in response to the detected events and automatically distribute electronic messages from a centralized system to a plurality of subsystems that traditionally often utilize unrelated, uncoordinated information systems.

BACKGROUND

Modern hospitals treat hundreds of patients every day. When a patient arrives, their condition and needs must be evaluated and addressed quickly, often requiring the coordination and communication of multiple departments in the hospital. In many situations, the incoming patient must be placed in the proper area of the hospital, and placement is often affected by hospital bed status and availability. Beds typically become available once a previous patient is discharged from the hospital, and one or more teams clean and treat the hospital bed room. Accomplishing these discharge and cleaning processes requires frequent and constant exchange of data and information throughout the hospital between disparate departments.

Traditional communication techniques for event detection and communication in such environments are based upon outdated communication technologies, resulting in overloaded systems that are slow, error-prone, and do not provide facility-wide communication using a centralized system. Indeed, traditional techniques usually rely upon multiple disparate systems, which may not integrate and exchange information regarding discharges, cleaning team statuses, and bed availability for new patient placement.

Traditional techniques also involve telephone-based manual reporting of an event and/or manual requests for cleaning, usually through phone calls between individuals in the facility. For example, in traditional systems, a requester may place a telephone call to a phone number, and request a service or provides information about a status. The requester may speak with a computerized interactive voice response (IVR) system, which then processes the received information for review by a dispatcher to identify and direct a responder in response to the requester's information. Current systems rely solely on information received during a manual telephone call, which can be sporadic and/or untimely, and can include incorrect information. Moreover, because traditional systems rely on telephone calls and IVR-based processing, traditional systems often experience very high call volumes which strain communication networks in the facility. In many instances, unnecessary and redundant calls also increase network strain, and traditional systems usually result in overloaded telephone lines and missed requests, thereby degrading the quality and speed of room cleaning and patient placement.

In view of the technical deficiencies of current systems discussed above, there is a need for improved systems and methods centralized real-time event detection and communication.

SUMMARY

Disclosed embodiments relate to systems and methods for automated and centralized real-time event detection and communication. In some embodiments, events can include patient discharge activities that are detected via electronic input from one or more mobile devices or networked computer terminals, or via sensor data associated with a patient or patient equipment. Events may also include facility room treatments such as cleaning, maintenance, or other activities associated with post-discharge procedures for readying a room for new patients. Event information can include, for example, occupancy and discharge status, bed and room cleanliness triggers, and room maintenance triggers. Disclosed embodiments may provide for monitoring a plurality of parameters, schedules, milestones, and events associated with a patient discharge process, and automate electronic communications based on detected discharge events and other events associated with the bed turnaround process established for a given facility, by automating the generation and propagation of notifications and graphical user interfaces to multiple electronic devices that are traditionally associated with disparate teams. Consistent with some embodiments, a centralized server for event monitoring and automating electronic communications is disclosed. The centralized server may comprise at least one network interface for bidirectional communication with a plurality of mobile devices on at least one computer network, at least one processor communicatively connected to the at least one network interface, and a storage medium storing instructions. When executed, the at least one processor is configured to perform operations including: receiving, via the at least one network interface, event information indicative of at least one discharge event associated with one or more individuals assigned to one or more rooms; automatically identifying a department associated with the one or more rooms in the received event information; automatically receiving, from one or more databases connected to the at least one computer network, cleaning protocol information for the identified department; identifying, in the received cleaning protocol information, one or more milestones to be completed; automatically generating workload data indicating a workload amount proportionate to the identified milestones; receiving, from the one or more databases, electronic device contact information and assignment information for a plurality of individuals associated with the cleaning protocol information; comparing the assignment information and the workload data to identify a first individual capable of completing the one or more milestones; automatically assigning the one or more milestones to the first individual; automatically identifying, in the electronic device contact information, a first mobile device associated with the first individual; and automatically generating a first electronic notification addressed to the first mobile device, the first electronic notification including information associated with the at least one discharge event and the one or more milestones.

Consistent with some embodiments, a computerized system is disclosed. The computerized system may include at least one processor and a storage medium storing instructions that when executed, cause the at least one processor to provide for display a graphical user interface, by: receiving, from one or more databases, a first set of data related to discharges of the department; receiving, from the one or more databases, a second set of data related to routine cleaning of the department; determining one or more workload requirements based on the first set of data and the second set of data; receiving, from the one or more databases, staffing data related to the department; determining, by the at least one processor, whether an employee in the staffing data meets the one or more workload requirements; automatically assigning, based on the determination, one or more tasks associated with the workload requirements to the employee; and generating a graphical user interface reflecting the automatic assignment.

Consistent with some embodiments, a centralized server-based method for event monitoring and automating electronic communications is disclosed. The method may comprise: receiving, by at least one processor via at least one network interface to at least one computer network, event information indicative of at least one discharge event associated with one or more individuals assigned to one or more rooms, automatically identifying a department associated with the one or more rooms in the received event information, automatically receiving, from one or more databases connected to the at least one computer network, cleaning protocol information for the identified department, identifying, in the received cleaning protocol information, one or more milestones to be completed, automatically generating workload data indicating a workload amount proportionate to the identified milestones, receiving, from the one or more databases, electronic device contact information and assignment information for a plurality of individuals associated with the cleaning protocol information, comparing the assignment information and the workload data to identify a first individual capable of completing the one or more milestones, automatically assigning the one or more milestones to the first individual, automatically identifying, in the electronic device contact information, a first mobile device associated with the first individual, and automatically generating a first electronic notification addressed to the first mobile device, the first electronic notification including information associated with the at least one discharge event and the one or more milestones.

Consistent with some embodiments, a computerized method is disclosed. The computerized method may include receiving, by a processor from one or more databases, a first set of data related to discharges of the department; receiving, by the processor the one or more databases, a second set of data related to routine cleaning of the department; determining, by the processor, one or more workload requirements for the first set of data and the second set of data; receiving, by the processor from the one or more databases, staffing data related to the department; determining, by the processor, whether an employee in the staffing data meets the one or more workload requirements; automatically assigning, by the processor and based on the determination, one or more tasks associated with the workload requirements to the employee; and generating a graphical user interface reflecting the automatic assignment.

Consistent with other disclosed embodiments, non-transitory computer-readable storage media may store program instructions, which are executed by at least one processor device and perform any of the methods described herein.

The foregoing general description and the following detailed description are exemplary and explanatory only and are not restrictive of the claims.

BRIEF DESCRIPTION OF THE DRAWINGS

The accompanying drawings, which are incorporated in and constitute a part of this specification, illustrate several embodiments and, together with the description, serve to explain the disclosed principles. In the drawings.

DETAILED DESCRIPTION

Reference will now be made in detail to exemplary embodiments, examples of which are illustrated in the accompanying drawings and disclosed herein. Wherever convenient, the same reference numbers will be used throughout the drawings to refer to the same or like parts.

Figure 1:
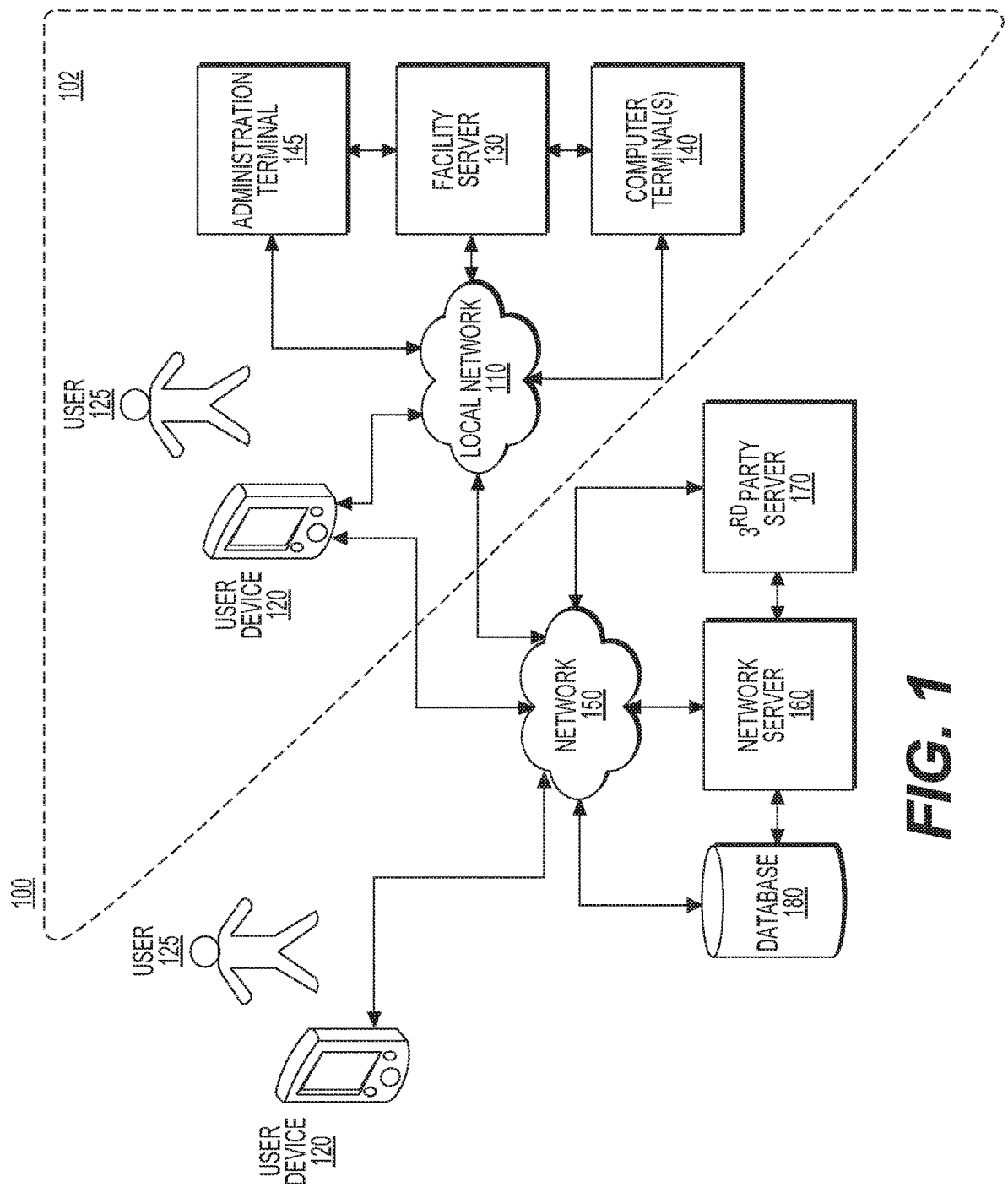
FIG. 1 depicts an example of a system environment for generating interactive graphical user interfaces, consistent with embodiments of the present disclosure.

FIG. 1 shows a diagram of a load balancing and workflow management system 100 that may be configured to perform one or more software processes that, when executed by one or more processors, perform methods consistent with disclosed embodiments. The components and arrangements shown in FIG. 1 are not intended to limit the disclosed embodiments, as the components used to implement the disclosed processes and features may vary.

As shown in FIG. 1, system 100 may include a facility server 130, a computer terminal 140, an administration terminal 145, a user device 120, network server 160, third party server 170, and database 180. The components of system 100 may communicate directly, through network 150, through local network 110, or through a combination of communications methods. In some embodiments, local network 110, facility server 130, computer terminal 140, administrator terminal 145, and user device 120 may be physically disposed within a facility such as a hospital or office building (e.g. a facility system 102) while network 150, network server 160, third party server 170, and database 180 may be external to the workplace. Other components known to one of ordinary skill in the art may be included in system 100 to perform tasks consistent with the disclosed embodiments. For example, in some embodiments, facility system 102 may include one or more sensor devices located throughout the facility to monitor one or more conditions such as occupancy, temperature, humidity, proximity, and other parameters indicative of a status or condition of a bed, room, area, equipment, or supplies. Additionally, in some embodiments facility system 102 may include one or more wireless receivers (not shown) configured to detect one or more wireless sensors or locating tags, to track a location of a tagged item and/or person, or a condition about the tagged item and/or person.

Computer terminal 140 may be a standalone device disposed in an office, a room, an employee station, or an alternative central location in a workplace. In some embodiments, computer terminal 140 may be a desktop or notebook computer, a flat panel or projected display, or any other display. In some embodiments, computer terminal 140 may be associated with a particular room in a facility, such as a particular patient room, hotel room, conference room, or any other type of room. Thus, a message received from a computer terminal 140 may automatically associate the message with the room in which computer terminal 140 is installed.

Administrator terminal 145 may include a computer system or a device associated with a user 125 that manages or oversees a portion of facility system 102. For example, administrator terminal 145 may comprise a computer system located at a head nurse station, a housekeeping manager's office, or any other department manager's office or station.

User 125 may be one or more individuals associated with the patient. Users 125 may operate computer terminal 140, user device 120, and/or another computer (not shown) to interact with system 100. Users 125 may be individuals located within and/or outside of the facility system 102. For example, users 125 may include physicians and nurses within the facility responsible for transferring the patients to different units. Users 125 may also include one or more individuals who are responsible for responding to task requests, such as cleaning and transportation of the patients. Users 125 may further include individuals outside of facility system 102, such as people with personal relationships with the patients (e.g. family members) and referring individuals (e.g. outside physicians and medics).

System 100 may be customizable and provide individualized access for each of the users 125. For example, in some embodiments, only certain users 125, such as physicians and nurses, may be allowed to generate transfer requests. In some embodiments, one or more users 125, such as the patient's primary physician, may be required to authorize all requests. Users 125 solely responsible for specific tasks may have access limited to perform their responsibilities. It is also contemplated that some users 125, such as family members, may have read-only access.

User device 120 may be a personal computing device such as, for example, a general purpose or notebook computer, a mobile device with computing ability, a tablet, smartphone, wearable device such as Google Glass™ or smart watches, or any combination of these computers and/or affiliated components. In some embodiments, user device 120 may be a computer system or mobile computer device that is operated by user 125. In some embodiments, user device 120 may be associated with a particular individual such as user 125, such that messages and/or task assignments directed toward user 125 are sent to user device 120. In some embodiments, user device 120 may communicate with facility server 130 and/or network server 160 via direct wireless communication links (not shown), or via a combination of one or more of local network 110 and/or network 150.

Facility server 130 may be operated by a facility such as a hospital. Facility server 130 may enable communication within a computer-based system including computer system components such as desktop computers, workstations, tablets, hand held computing devices, memory devices, and/or internal network(s) connecting the components.

Network 150 may comprise any type of computer networking arrangement used to exchange data. For example, network 150 may be the Internet, a private data network, virtual private network using a public network, and/or other suitable connection(s) that enables system 100 to send and receive information between the components of system 100. Network 150 may also include a public switched telephone network ("PSTN") and/or a wireless cellular network.

Local network 110 may comprise any type of computer networking arrangement used to exchange data in a localized area, such as WiFi, Bluetooth™, Ethernet, and other suitable short-range connections that enable computer terminal 140 and user device 120 to send and receive information between the components of system 100. In some embodiments, local network 110 may be excluded, and computer terminal 140 and user device 120 may communicate with system 100 components via network 150. In some embodiments, computer terminal 140 and/or user device 120 may communicate with one or more system 100 components via a direct wired or wireless connection.

Network server 160, third party server 170, and database 180 may be one or more servers or storage services provided by an entity such as a provider of networking, cloud, or backup services. For example, in some embodiments, network server 160 may be associated with a cloud computing service such as Microsoft Azure™ or Amazon Web Services™. In such embodiments, network server 160 may comprise a plurality of geographically distributed computing systems executing software for performing one or more functions of the disclosed methods. Additionally, in some embodiments, third party server 170 may be associated with a messaging service, such as, for example, Apple Push Notification Service™, Azure Mobile Services™, or Google Cloud Messaging™. In such embodiments, third party server 170 may handle the delivery of messages and notifications related to functions of the disclosed embodiments, such as task creation, task assignment, task alerts, and task completion messages and notifications.

In some embodiments, system 100 may include configurations that vary from the example shown in FIG. 1, which illustrates a facility system 102 working in concert with a cloud computing system including network server 160, third party server 170, and database 180. As a first variation, system 100 may include only facility system 102, and thus may exclude cloud computing components such as network server 160, third party server 170, and database 180. In such embodiments, facility system 102 may handle substantially all operations and functions of the present embodiments. As a second variation, system 100 may exclude components of facility system 102 such as facility server 130. In such embodiments, a cloud computing system including network server 160, third party server 170, and/or database 180 may handle some or all computing and message-related functions of the disclosed embodiments.

Figure 2:
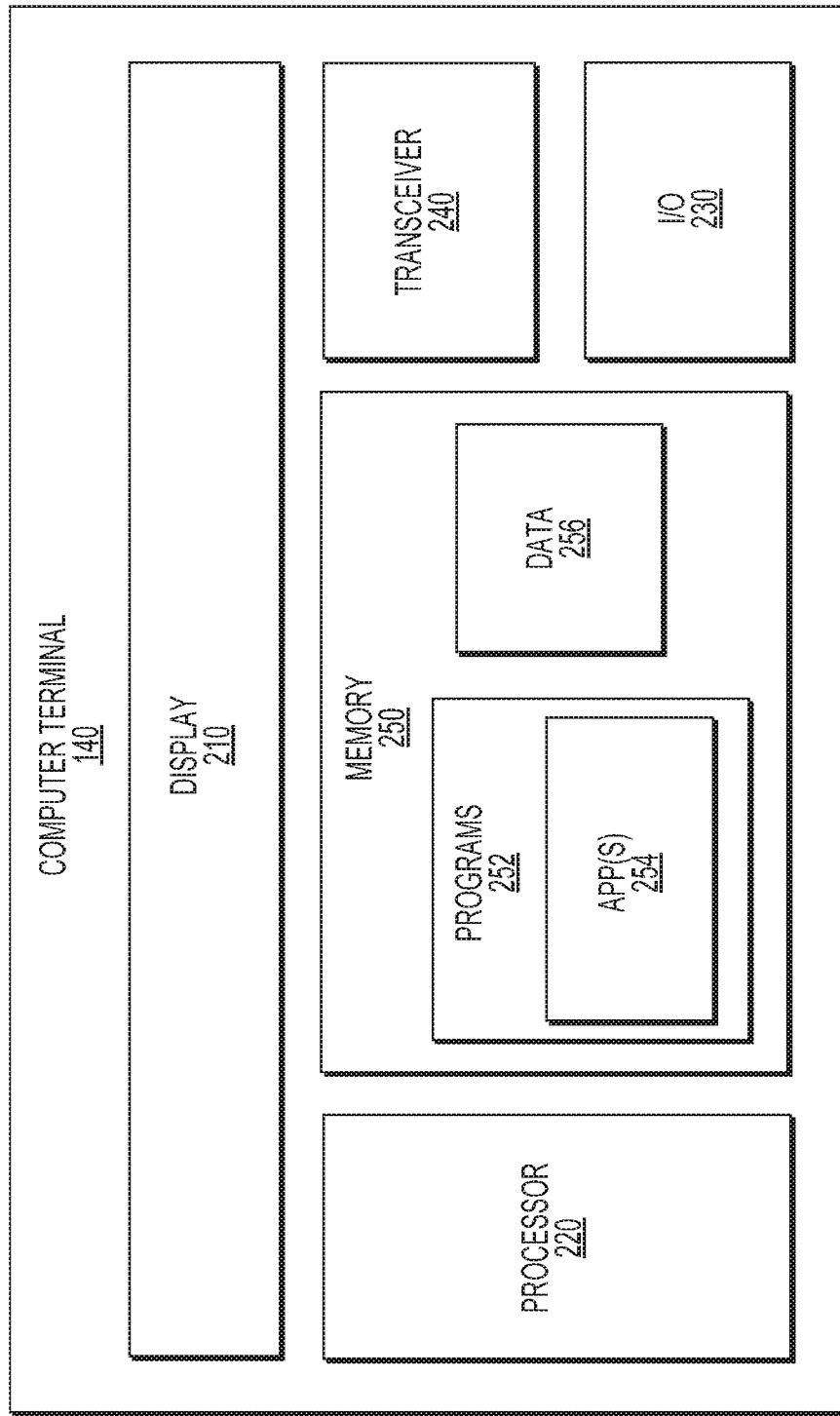
FIG. 2 depicts an example of a computer terminal, consistent with embodiments of the present disclosure.

FIG. 2 shows a diagram of computer terminal 140, consistent with disclosed embodiments. As shown, computer terminal 140 may include a display 210, one or more processors 220, input/output ("I/O") devices 230, a transceiver 240, and memory 250.

Display 210 may include one or more screens for displaying task management information such as, for example, liquid crystal display (LCD), plasma, cathode ray tube (CRT), or projected screens Processor 220 may be one or more known processing devices, such as microprocessors manufactured by Intel™ or AMD™ or licensed by ARM. Processor 220 may constitute a single core or multiple core processors that executes parallel processes simultaneously. For example, processor 220 may be a single core processor configured with virtual processing technologies. In certain embodiments, processor 220 may use logical processors to simultaneously execute and control multiple processes. Processor 220 may implement virtual machine technologies, or other known technologies to provide the ability to execute, control, run, manipulate, store, etc. multiple software processes, applications, programs, etc. In another embodiment, processor 220 may include a multiple-core processor arrangement (e.g., dual, quad core, etc.) configured to provide parallel processing functionalities to allow computer terminal 140 to execute multiple processes simultaneously. One of ordinary skill in the art would understand that other types of processor arrangements could be implemented that provide for the capabilities disclosed herein.

I/O devices 230 may include one or more devices that allow computer terminal 140 to receive input from one or more users 125. I/O devices 230 may include, for example, one or more pointing devices, keyboards, buttons, switches, touchscreen panels, cameras, barcode scanners, radio frequency identification (RFID) tag reader, and/or microphones.

Transceiver 240 may include one or more communication modules for establishing communication between computer terminal 140 and other devices of system 100 via, for example, local network 110 and/or network 150. For example, transceiver 240 may include circuitry and one or more antennas for communicating wirelessly with local network 110 using a short range/near-field wireless communication protocol such as Bluetooth™, Bluetooth™ LE, WiFi, and Zigbee™. Further, transceiver 240 may communicate with network 150 and/or local network 110 using any known network protocol including any form of wired or wireless internet access.

Memory 250 may include a volatile or non-volatile, magnetic, semiconductor, tape, optical, removable, non-removable, or other type of storage device or tangible (i.e., non-transitory) computer-readable medium that stores one or more program(s) 252, such as app(s) 254, and data 256. Data 256 may include, for example, hospital information, patient information, user information, task information, and display settings and preferences. For example, data 256 may include task assignments and staff scheduling. In some embodiments, data 256 may include one or more rule sets for load balancing staff scheduling.

Program(s) 252 may include operating systems (not shown) that perform known operating system functions when executed by one or more processors. By way of example, the operating systems may include Microsoft Windows™, Unix™, Linux™, Apple™ operating systems, Personal Digital Assistant (PDA) type operating systems, such as Microsoft CE™, or other types of operating systems. Accordingly, disclosed embodiments may operate and function with computer systems running any type of operating system. Computer terminal 140 may also include communication software that, when executed by a processor, provides communications with network 150 and/or local network 110, such as Web browser software, tablet, or smart hand held device networking software, etc.

Program(s) 252 may also include app(s) 254, such as a load balancing and workflow management app, which when executed causes computer terminal 140 to perform processes related to managing, prioritizing, and scheduling patient information and tasks. For example, app(s) 254 may configure computer terminal 140 to perform operations including receiving information pertaining to a task of one or more departments, receiving staffing information, displaying staffing information, monitoring patient statuses, assigning tasks to employees, displaying employee assignments, and monitoring task statuses.

Figure 3:
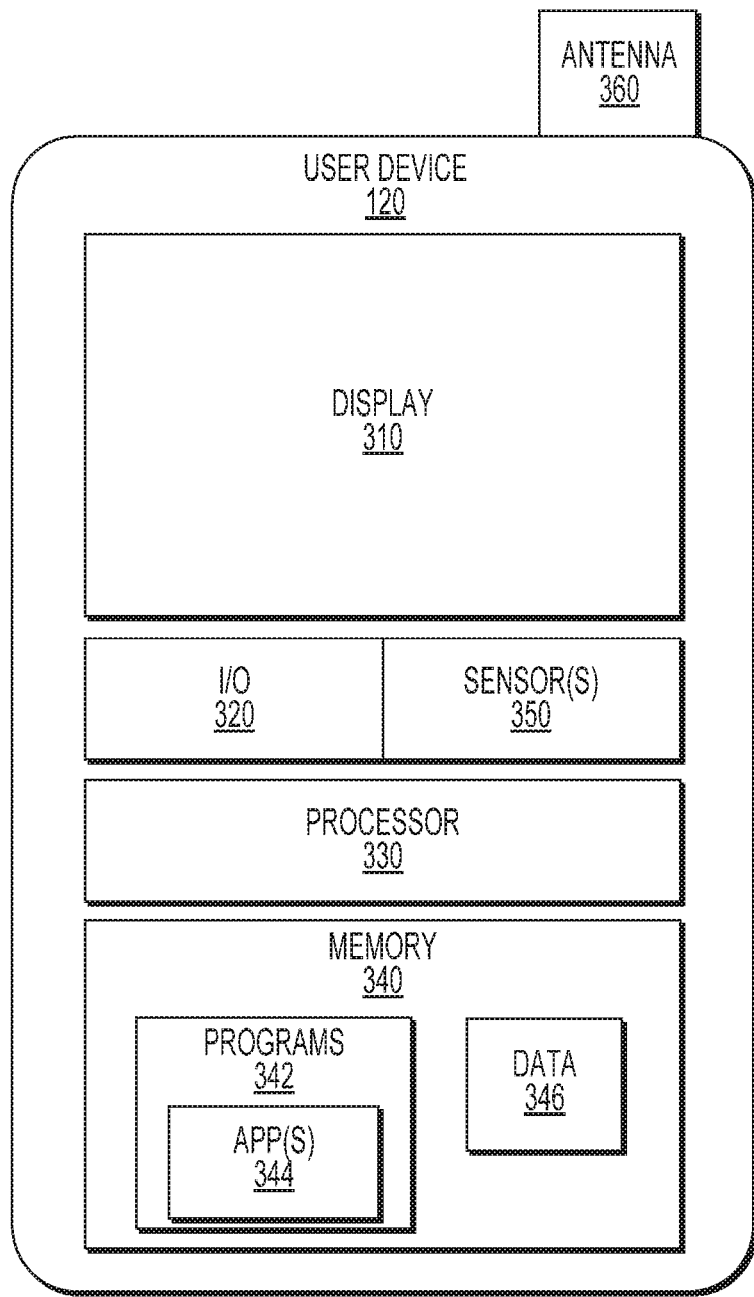
FIG. 3 depicts an example of a user device, consistent with embodiments of the present disclosure.

FIG. 3 shows a diagram of an exemplary user device 120, consistent with disclosed embodiments. As shown, user device 120 may include display 310, I/O device(s) 320, processor 330, memory 340 having stored thereon data 346 and one or more programs 342, such as app(s) 344, sensor(s) 350, and antenna 360.

Display 310 may include one or more devices for displaying information, including but not limited to, liquid crystal displays (LCD), light emitting diode (LED) screens, organic light emitting diode (OLED) screens, and other known display devices.

I/O devices 320 may include one or more devices that allow mobile device 120 to send and receive information. I/O devices 320 may include, for example, a pointing device, keyboard, buttons, switches, and/or a touchscreen panel. I/O devices 320 may also include one or more communication modules (not shown) for sending and receiving information via antenna 360 from other components in system 100 by, for example, establishing wired or wireless connectivity between mobile device 120 to local network 110, network 150, or by establishing direct wired or wireless connections between user device 120 and other components of system 100. Direct connections may include, for example, Bluetooth™, Bluetooth LE™, WiFi, near field communications (NFC), or other known communication methods which provide a medium for transmitting data between separate devices.

Processor(s) 330 may be one or more known computing devices, such as those described with respect to processor 220 in FIG. 2.

Memory 340 may be a volatile or non-volatile, magnetic, semiconductor, tape, optical, removable, non-removable, or other type of storage device or tangible (i.e., non-transitory) computer-readable medium such as those described with respect to memory 250 in FIG. 2.

In some embodiments, user device 120 may contain one or more sensors 350 for collecting environmental, movement, and/or security data. Sensors 350 may include: one or more environmental sensors such as, for example, ambient light sensors, microphones, temperature sensors, and humidity sensors; motion detectors such as, for example, GPS receivers, location-based data receivers, accelerometers, and gyroscopes; and security sensors such as, for example, fingerprint readers, retina scanners, and other biometric sensors capable of use for security and individual identification. In some embodiments, processor 330 may use data collected by sensors 350 to control or modify functions of program(s) 342.

Figure 4:
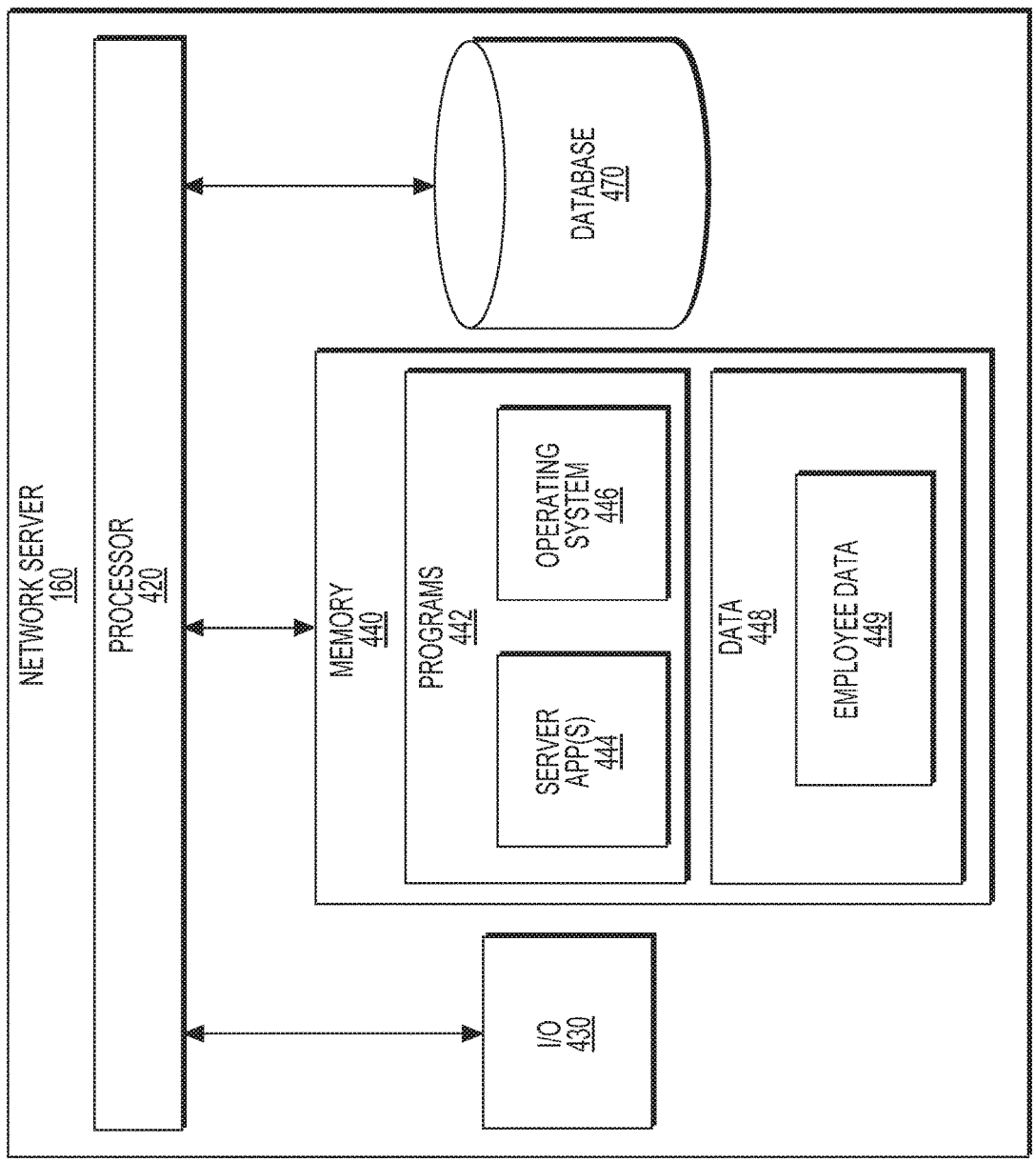
FIG. 4 depicts an example of a network server, consistent with embodiments of the present disclosure.

FIG. 4 shows a diagram of an exemplary network server 160, consistent with disclosed embodiments. In some embodiments, network server 160 may support or provide a cloud computing service, such as Microsoft Azure™ or Amazon Web Services™. In such embodiments, network server 160 may include one or more distributed computer systems capable of performing distributed computing functions and providing cloud computing services and functions consistent with disclosed embodiments. In some embodiments, network server 160 may operate in conjunction with facility server 130. In other embodiments, network server 160 may operate alone, and facility server 130 may be replaced by a network connection to network 150 and/or local network 110. In such embodiments, network server 160 may perform all functions associated with the disclosed methods. In other embodiments, facility server 130 may operate alone, without network server 160. In such embodiments, facility system 102 may operate as a standalone system, in which facility server 130 performs all functions associated with the disclosed methods. Those of ordinary skill in the art will appreciate that the computing arrangements are not limited to these examples, and that other embodiments may include one or more alternate configurations of computing systems capable of performing functions associated with the disclosed embodiments.

In some embodiments, network server 160 may connect to multiple facilities located in different geographical locations. In such embodiments, network server 160 may manage tasks that span across multiple facilities, such as transferring patients between facilities. Additionally, network server 160 may collect data from multiple units to evaluate performance times in different units, and improve the accuracy of expected completion times for different types of tasks using one or more data regression algorithms.

As shown in FIG. 4, network server 160 may include one or more processor(s) 420, input/output ("I/O") devices 430, memory 440 storing programs 442 (including, for example, server app(s) 444 and operating system 446) and data 448, and a database 470. Network server 160 may be a single server or may be configured as a distributed computer system including multiple servers or computers that interoperate to perform one or more of the processes and functionalities associated with the disclosed embodiments.

Processor(s) 420 may be one or more known computing devices, such as those described with respect to processor 220 in FIG. 2.

In some embodiments, network server 160 may also include one or more I/O devices 430 including interfaces for receiving signals or input from devices and providing signals or output to one or more devices that allow data to be received and/or transmitted by network server 160. For example, network server 160 may include interface components, which may provide interfaces to one or more input devices, such as one or more keyboards, mouse devices, and the like, that enable network server 160 to receive input from one or more user 125 that is associated with facility system 102.

In some embodiments, network server 160 may include one or more storage devices configured to store information used by processor 420 (or other components) to perform certain functions related to the disclosed embodiments. In one example, network server 160 may include memory 440 that includes instructions to enable processor 420 to execute one or more applications such as server applications and any other type of application or software known to be available on computer systems. Additionally or alternatively, the instructions, application programs, etc. may be stored in an internal database 470 or external database 180 (shown in FIG. 1) in communication with network server 160, such as one or more database or memory accessible over network 150. Database 470 or other external storage may be a volatile or non-volatile, magnetic, semiconductor, tape, optical, removable, non-removable, or other type of storage device or tangible (i.e., non-transitory) computer-readable medium.

In one embodiment, network server 160 may include memory 440 that includes instructions that, when executed by processor 420, perform one or more processes consistent with the functionalities disclosed herein. Methods, systems, and articles of manufacture consistent with disclosed embodiments are not limited to separate programs or computers configured to perform dedicated tasks. For example, network server 160 may include memory 440 that may include one or more programs 442 to perform one or more functions of the disclosed embodiments. Moreover, processor 420 may execute one or more programs located remotely from account information display system 100. For example, network server 160 may access one or more remote programs, that, when executed, perform functions related to disclosed embodiments.

Programs 442 stored in memory 440 and executed by processor(s) 420 may include one or more server app(s) 452 and operating system 454. Server app(s) 452 may incorporate one or more apps configured to receive input of patient discharges and cleaning information, estimate on-demand staffing requirements, automatically adjust scheduled staffing, and output the adjusted scheduled staffing to a user 125. In some embodiments, programs 442 may also include instructions that may be executed by processor 420 to perform real time locating systems (RTLS) through one or more wireless receivers of facility system 102. Processor 420 may be configured to utilize RTLS to identify and track tagged objects and people, and conditions of thereof. For example, objects and/or people may be equipped with a badge/tag that emits an RFID signal that may be detected by the wireless receivers of facility system 102. In some embodiments, processor 420 may detect the locations of patients and determine their statuses. For instance, processor 420 may determine that the patient is still occupying a bed when patient is located in or around the bed. Processor 420 may also determine if the patient has been discharged, for example, by determining that the patient is in a lobby of facility system 102 for a certain period of time. Processor 420 may also track employees (e.g., users 125) by tracking GPS data of user devices 120.

In some embodiments, memory 440 may store data 448 including data associated with hospitals, units, patients, employees, tasks, assets, assignment algorithms, and any other data related to the disclosed embodiments. For example, data 448 may include one or more entries including information pertaining to employees (e.g., users 125) including identification, scheduled work assignments, personal traits, capabilities, certifications, job titles, and preferences. Data may also include transactional data indicating, for example, the types of jobs that the employees have performed, and the start time, the end time, and the duration of performed jobs. Data may also include presence data indicating, for example, the location of the employees within facility system 102 at different time points according to RTLS data. In some embodiments, data 448 is stored in database 470, memory 440, memory 250, memory 340, database 180, and any combination thereof.

In some embodiments, memory 440 and database 470 may include one or more memory devices that store data and instructions used to perform one or more features of the disclosed embodiments. Memory 440 and database 470 may also include any combination of one or more databases controlled by memory controller devices (e.g., server(s), etc.) or software, such as document management systems, Microsoft SQL databases, SharePoint databases, Oracle™ databases, Sybase™ databases, or other relational databases.

Network server 160 may communicate with one or more remote memory devices (e.g., third-party server 170 and/or database 180) through network 150 or a different network (not shown). The remote memory devices may be configured to store information and may be accessed and/or managed by network server 160. By way of example only, the remote memory devices may be document management systems, Microsoft SQL database, SharePoint databases, Oracle™ databases, Sybase™ databases, or other relational databases. Systems and methods consistent with disclosed embodiments, however, are not limited to separate databases or even to the use of a database.

Figure 5:
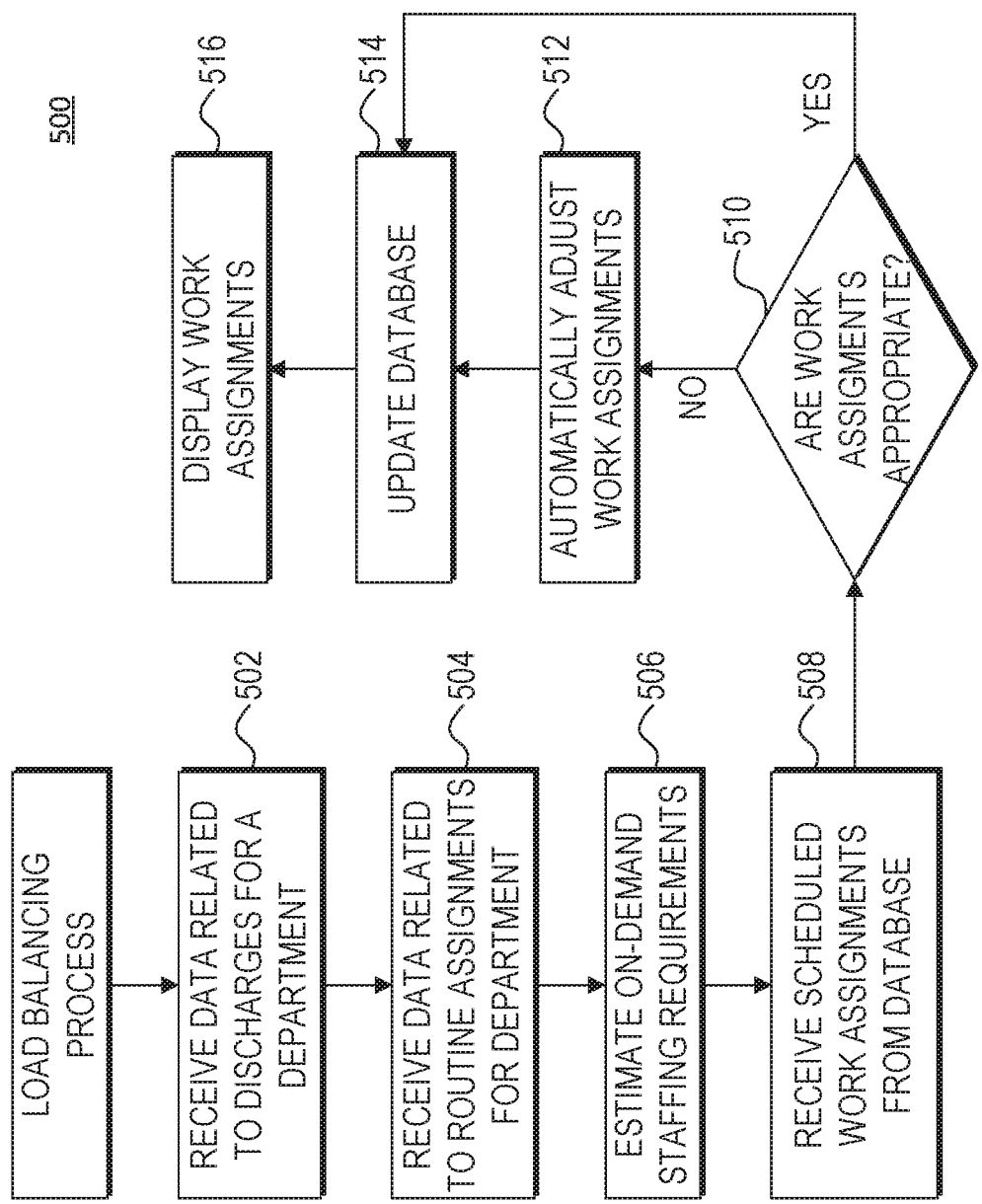
FIG. 5 is a flowchart of an example of a process for generating interactive graphical user interfaces for load balancing, consistent with embodiments of the present disclosure.

FIG. 5 shows a flowchart of an exemplary process for generating graphical user interfaces for load balancing 500. Process 500 may provide the advantage of properly staffing departments based on multiple different real-time staffing requirements across multiple departments and using data received from one or more computer systems, such as discharges, routine cleaning, and/or on-demand requirements. Process 500 may also advantageously provide communication between departments to alter work assignments for employees based on determined workloads. Furthermore, process 500 may optimize task assignments and outcomes based on historical performance as periodically established and validated per employee (e.g. user 125). Process 500 may be employed to periodically review workload assignments to employees among other conditions and assign or redistribute work when applicable to ensure that employees are neither overburdened nor underutilized and that departments are ensured adequate employee resources in appropriate amounts. Process 500 is described herein as performed primarily by network server 160, however in some embodiments, facility server 130, computer terminal 140, administration terminal 145, user device 120, and/or third party server 170 may perform one or more steps of process 500.

Process 500 may be performed with other applications and/or components, and receive data from a number of different sources. In some embodiments, process 500 may be used in conjunction with one or more app(s) performed by at least one of network server 160, facility server 130, computer terminal 140, administration terminal 145, user device 120, and/or third party server 170. For example, network server 160 may be configured to perform process 500 in conjunction with apps, such as real-time patient placement, bed tracking, and/or workflow. Accordingly, the data received in process 500 may be generated by the apps.

Process 500 may begin in step 502 when network server 160 receives and processes data related to discharge of occupants (e.g., patients) for one or more computers associated with one or more departments. The data may be received, for example, from an app executing on network server 160, or from an app executing on a device such as user device 120. In some embodiments, data may be received from a sensor device such as sensor 350. In some embodiments, the data may relate to a hospital department and include one or more patients that are scheduled to be discharged from the department, identity of the patients, and conditions of the patients. For example, the data may indicate any transmittable diseases (e.g., MRSA) of the patients that may require special accommodations or special cleaning considerations. The data may also include discharge assignments, such as number and location of beds to be cleaned, bed sheets to be replaced, and any additional requirements for each discharge assignment. In some embodiments, the data may be quantified based on the total time requirement for discharge assignments of each department. For example, the time requirement may factor in any additional time required for a discharge assignment following occupancy of a patient with MRSA. The time requirement may include additional steps of a protocol of treating the room and/or surrounding areas based on conditions. For instance, the protocol for reducing spread of the transmittable disease may include ultraviolet irradiation of the bed and any surrounding areas, regular cleaning, additional inspection, and/or additional cleaning steps. In some embodiments, the time requirement may also include transition times between each assignment. For example, a discharge assignment including the cleaning of first and second beds that are located further from each other may require additional transition time.

In step 504, network server 160 may receive and process data related to routine assignments for the one or more departments. In some embodiments, the data may be received from another application (e.g., a bed placement application) executed by network server 160 or another computer system. The data related to routine cleaning may include a list or protocol of one or more tasks or milestones in a routine, and a time requirement based on the current occupancy of the department. For example, the data may include time requirements for certain tasks and services, such as mopping floors, cleaning rooms and/or cleaning bathrooms. The number of services may be based on the number of occupants, occupied beds, and/or occupied rooms that need to be cleaned. For example, the data related to daily cleaning may exclude any unoccupied rooms where there is no cleaning required.

In step 506, network server 160 may estimate on-demand staffing requirements for the one or more departments. In some embodiments the on-demand staffing requirements may include time requirements for unscheduled work assignments. For example, network server 160 may account for variables such as unscheduled patients and/or cleaning requirements (e.g., spills and accidents). Network server 160 may also account for variables such as the current occupancy of the department and the nature of the department. For example, a larger number of occupancies may correspond to increased time requirements of spills and accidents due to the larger frequency of unscheduled cleaning requirements. Furthermore, network server 160 may also account for variables according to the department. For instance, some departments (e.g., an emergency room or ICU) may expect more unscheduled patients and/or spills and accidents than other departments (e.g., internal medicine). Accordingly, in some embodiments, network server 160 may estimate the on-demand staffing requirements by executing software stored in database 470. The software may include look-up charts, statistical distributions, and/or algorithms based on the determined variables. Network server 160 may also utilize computer learning algorithms for determining and continuously refining statistics. For example, network server 160 may receive real-time data of the actual correlation of the variables and on-demand schedule requirements, and update the software based on analyses of the real-time data.

In step 508, network server 160 may receive and process scheduled work assignments for the one or more departments from a database. The work assignments data may be stored in one or more of database 180, memory 250, and/or memory 340. The work assignment data may include, for example, dates and times that employees are scheduled to perform work assignments. The scheduled work data may also include identities of the one or more scheduled employees, capabilities of the employees, the assigned department(s), and/or the assigned duties and tasks. In some embodiments, the scheduled work assignments may be received from a scheduling app executed by one or more of user device 120, computer terminal 140, and/or third party server 170.

Network server 160 may process the received scheduled work assignments to determine the capabilities of the scheduled staff. For example, network server 160 may determine the capabilities by quantifying the workload capable of the scheduled staff, for example, according to data from look-up charts, statistical distribution, and/or algorithms. For instance, network server 160 may determine the work rate that each employee performs tasks, such as a discharge assignment, and determine the total number of tasks that the collective staff can perform in a specific period of time. Network server 160 may also determine the amount of additional related work that the employee may perform based on the scheduled tasks. For example, an employee working at a desk may have availability to clean up a spill or accident, while an employee scheduled for tasks in an operating room may not.

In step 510, network server 160 may determine whether the scheduled work assignments are appropriate for the requirements of each department. In some embodiments, network server 160 may compare the requirements of the department from steps 502-506 with the capabilities of the schedule staff from step 508. For example, if network server 160 determines that the requirements of the department exceed the capabilities of the scheduled staff, network server 160 may determine that additional scheduled staff is required for the department. On the other hand, if network server 160 determines the requirements of the department are less than the scheduled workload, network server 160 may determine the staff of the department may be reduced. Network server 160 may determine step 510 based on tolerances. For example, network server 160 may determine that the scheduled work assignments are appropriate if the scheduled work assignments exceed the requirements of each department by a 5-10% clearance. If network server 160 determines that the work assignments are appropriate ("YES"; step 510), process 500 may proceed to step 514. If the scheduled staffing appropriate is determined to be inappropriate ("NO"; step 510), network server 160 may proceed to step 512.

In step 512, network server 160 may automatically adjust the scheduled work assignments based on the scheduled staffing data. In some embodiments, network server 160 may modify the schedule of a department by adding/subtracting scheduled work assignments of step 508 based on the department requirements of steps 502-506. In some embodiments, network server 160 may compare the scheduled work assignments between different departments, for example, in the same hospital. For example, if network server 160 determines a first department lacks scheduled employees and a second department has excessive scheduled employees, network server 160 may mutually adjust the work assignments for each of the first and second departments. For instance, network server 160 may modify one or more work assignments of the second department by reassigning one or more employees to the first department. Network server 160 may also alter work assignments for one or more scheduled employees based on capability. For example, if network server 160 determines that there are excessive scheduled work assignments for processing discharges, network server 160 may alter the work assignment for one or more employees to perform routine cleaning or desk duty. In some embodiments, network server 160 may adjust work assignments based on availability or lack thereof of specialized or otherwise preferred employees. For example, a task related to moving a piece of equipment may be assigned or reassigned to an equipment delivery specialist, if available, and to a more general employee if no equipment delivery specialist is available. This scenario may arise for example, in a hospital with different staffing during day and night shifts. The hospital may have specialized employees available at one time in a day (e.g., during the daytime) and fewer, less specialized employees available at another time in a day (e.g., during the nighttime)

In step 514, network server 160 may update the work assignment data on the database. In step 516, network server 160 may generate one or more graphical user interfaces to display the updated work assignment data from the database. In some embodiments, network server 160 may generate a graphical user interface (GUI) to be displayed, for example, on user device 120 and/or computer terminal 140. For instance, network server 160 may display the GUI on display 210, 310 to one or more user(s) 125. Network server 160 may provide the data for display in the GUI based on accessed permissions for user 125. For example, network server 160 may display data to users 125 based on the work assignments of the specific user 125. Network server 160 may also display more data to other users 125, such as supervisors, based on accessed permissions. In some embodiments, the updated work assignment data may be transmitted in other forms, such as through an audio output of user device 120 and/or computer terminal 140. In some embodiments, the displayed GUI may include interactive elements, to allow users 125 to select specific work assignments and see additional data, or to make adjustments to work assignments. In some embodiments, the displayed GUI may be formatted for a mobile device such as user device 120.

Figure 6:
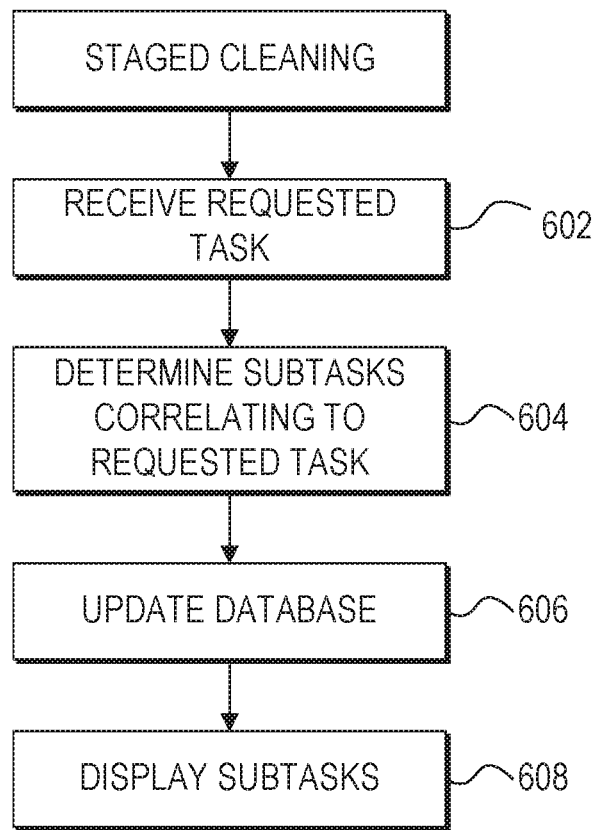
FIG. 6 is a flowchart of an example of a process for generating interactive graphical user interfaces for staged cleaning work, consistent with embodiments of the present disclosure.

FIG. 6 shows a flowchart of an exemplary process for generating graphical user interfaces for staged cleaning 600. Process 600 may provide the advantage of ensuring that required subtasks are performed in response to certain task requests. In some cases, process 600 may automatically schedule subtasks that may reduce the possible spread of infectious diseases. Process 600 is described herein as performed primarily by network server 160, however in some embodiments, facility server 130, computer terminal 140, administration terminal 145, user device 120, and/or third party server 170 may perform one or more steps of process 500.

Process 600 may begin in step 602 when network server 160 may receive and process a requested task. The task request may be received from user 125 via user device 120 and/or computer terminal 140. The task may relate to any number of objects. For example, the task may relate to cleaning tasks in a hospital environment.

In step 604, network server 160 may determine subtasks correlating to the requested task. In some embodiments, network server 160 may access data (e.g., from look-up charts) stored in one or more of database 180, memory 250, memory 340, and database 470. Network server 160 may process the requested task by accessing hospital and/or patient information related to the requested task. Network server 160 may also determine whether the requested task corresponds to one or more predetermined tasks of a look-up chart. The look-up chart may provide one or more subtasks that correspond to the requested tasks based on the patient and/or hospital information. Process 600 may have a particular advantage for the cleaning process in a hospital environment. For example, network server 160 may receive a requested task related to cleaning an area of a hospital. The area may include one or more rooms and/or beds that were previously occupied by a patient. Network server 160 may access patient information including one or more conditions (e.g., transmittable diseases) that need to be considered for the cleaning. Network server 160 may also access a look-up chart to determine whether the requested task and/or condition(s) trigger any additional subtasks. For example, based on a patient having MRSA, the network server 160 may access subtasks via look-up chart, including one or more of ultraviolet irradiation of the bed and any surrounding areas, regular cleaning, additional inspection, and/or additional cleaning steps.

In step 606, network server 160 may automatically update the work assignment data of the database with the subtasks of step 604. For example, network server may replace the requested task (e.g., cleaning a bed of a patient with MRSA) with subtasks, such as one or more of ultraviolet irradiation of the bed and any surrounding areas, regular cleaning, additional inspection, and additional cleaning steps. In some embodiments, network server 160 may generate and maintain a functional relationship between the subtasks to ensure coordinated performance. For example, the scheduling of a second subtask may depend on the duration of a first subtask, such that, network server 160 may introduce a delay in the commencement of the second subtask upon perceiving a delay in the completion of the first subtask. In some embodiments, network server 160 may assign subtasks to one or more employees based on data 448 (e.g., scheduling, capabilities, certifications, job titles, RTLS data). For example, network server 160 may assign a first subtask to one or more first employee(s) and a second subtask to one or more second employee(s). As a more specific example, a requested task of cleaning a bed of a patient with MRSA may be replaced with subtasks such as ultraviolet disinfection, standard cleaning, curtain removal, and room inspection. Assignment of these subtasks may be divided among two or more employees, or the tasks may be assigned separately, each task to a different employee. In step 608, network server 160 may output the updated work assignment data. The updating and outputting of the work assignment data may be performed similar to steps 514-516.

Figure 7:
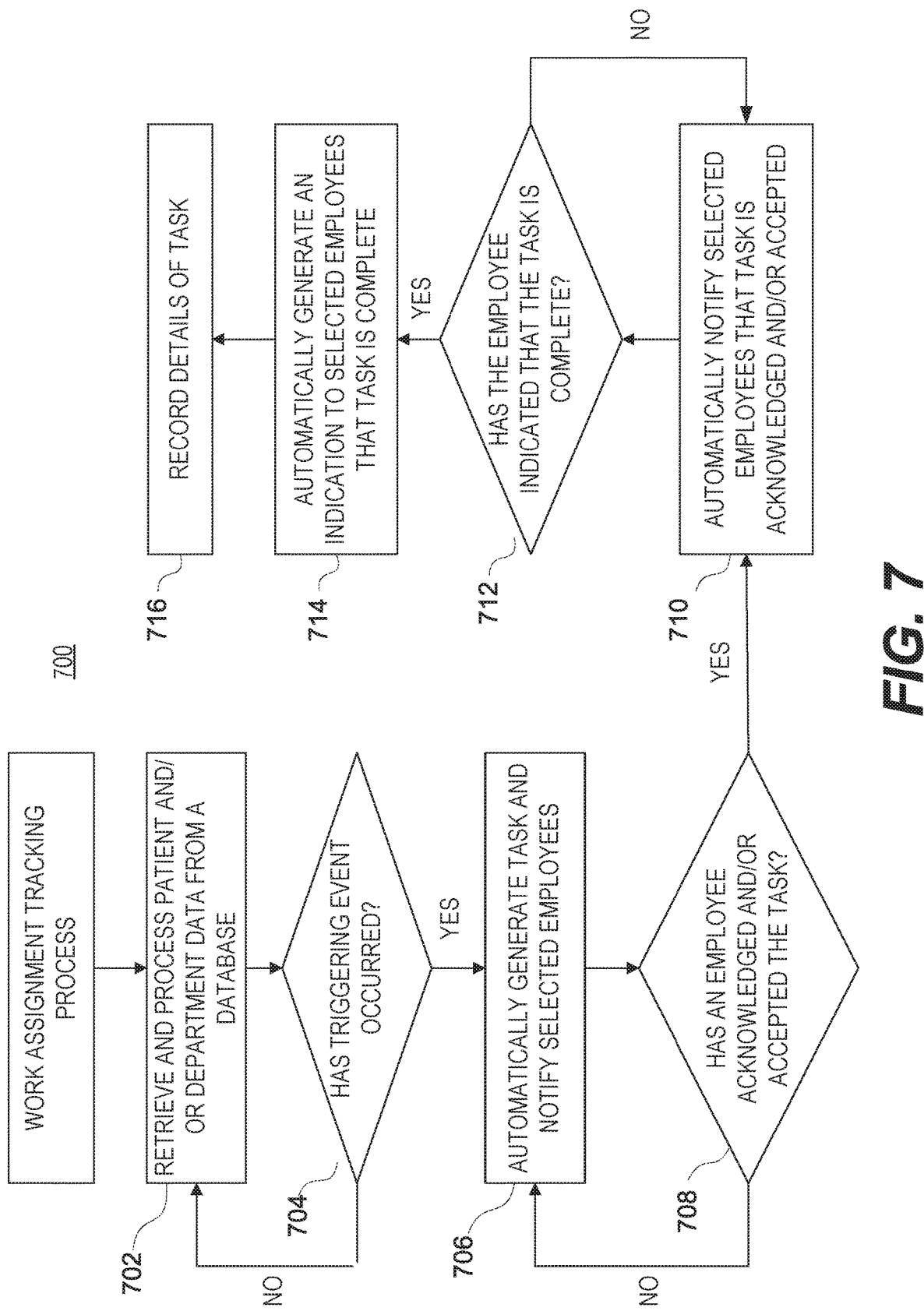
FIG. 7 is a flowchart of an example of a process for generating interactive graphical user interfaces for work assignment tracking, consistent with embodiments of the present disclosure.

FIG. 7 shows a flowchart of an exemplary process for generating graphical user interfaces for tracking a work assignment 700. Process 700 may be used in conjunction with other processes, such as a real-time patient placement process. In some embodiments process 700 may be applied to discharge assignments of one or more departments, including assigned bed cleaning after a patient has been discharged. Process 700 may enhance efficiency during discharge of the patients and improve capacity for patient placement by providing a comprehensive display of real-time data concerning multiple factors and from multiple sources. Process 700 is described herein as performed primarily by network server 160, however in some embodiments, facility server 130, computer terminal 140, administration terminal 145, user device 120, and/or third party server 170 may perform one or more steps of process 700. Even though process 700 is described with regard to cleaning beds, it is also contemplated that process 700 may also be adapted to other manual activities such as patient transportation.

In step 702, network server 160 may retrieve and process patient and/or department data from a database and/or a computer device such as user device 120. In some embodiments, network server 160 may access data related to discharge assignments stored in one or more of database 470, memory 440, memory 250, memory 340, database 180, and any combination thereof. For example, the data may include the number and/or location of a plurality of beds to be cleaned in one or more departments of the hospital. The data may include scheduled patient occupants of the beds and patient information of the occupying patients. For example, the patient information may include the identification of the patient, a status of the patient, and/or any scheduled bed occupations or discharges. In some embodiments, network server 160 may further receive data from a sensor device such as sensors 350, such as a real-time locating system device or an occupancy sensor installed in a bed or room. For example, network server 160 may be configured track an RFID badge associated with one or more patients to determine an occupancy status or location of the patients. Network server 160 may also be configured to track an RFID badge of employees and/or tags on equipment. For example, network server 160 may be configured to track equipment within facility system 102 and/or detect bed occupancy by real-time data received from a weight sensor in a bed.

In step 704, network server 160 may continually monitor the received data to determine whether a triggering event occurs, such as the change of a status of the patients and/or beds. For example, network server 160 may determine whether the expected discharge of any of the patients has occurred, and/or whether an employee has indicated the status of a bed has changed. For instance, user 125 may indicate that a discharge has occurred via one or more of user device 120 and/or computer terminal 140. In some embodiments, network server 160 may determine the change in status of a bed by determining the location and/or status of the patient assigned to the bed. For example, using collected data from one or more location or occupancy sensors, network server 160 may determine that an RFID badge has been removed from a patient and/or the patient has been in a lobby of a hospital (e.g., facility system 102) for a predetermined time period. Network server 160 may determine that, based on the location/occupancy data satisfying one or more conditions or exceeding one or more rules, the patient is being discharged from the hospital, and the bed to which the patient was assigned is now unoccupied and ready for cleaning. Further triggering events may include receipt of an order for treatment (such as infusion therapy, a procedure, or a test) or an inventory status change such as an inventory crossing a threshold, for instance a Par level variance in a clean utility room. If network server 160 determines that a trigger event has not occurred ("NO"; step 704), network server 160 may continually retrieve and processing data according to step 702. However, if network server 160 determines that a trigger event has occurred ("YES"; step 704), network server 160 may proceed to step 706.

In step 706, network server may automatically generate one or more tasks and notify selected employee(s) (e.g., user(s) 125). In some embodiments, network server 160 may generate a discharge assignment and automatically notify selected user(s) 125 of the discharge assignment. The selected user(s) 125 may include one or more user(s) 125 that are responsible for the task (e.g., managing the discharge assignment). The selected user(s) 125 may be notified in a number of different manners, including a call, a text message, a push notification, a message within an app, and/or an email. Network server 160 may transmit the notification to user(s) 125 through one or more of user device 120, computer terminal 140, an intercom, and/or a station phone of facility system 102. In some embodiments, network server 160 may generate or update a GUI notifying user(s) 125 of the task. Network server 160 may send updates and reminders to the user(s) by generating or updated the GUI. Network server 160 may also recalculate or update the determination of selected user(s) 125 based on events, such as lack of acceptance from previously selected user(s) 125.

In some embodiments, network server 160 may be configured to create a division of labor by selecting user(s) 125 based on the task being located in an area of the department and/or hospitals. For example, network server 160 may assign user(s) 125 responsibilities for a certain number of beds in close proximity, or for beds of an entire department. Network server 160 may assign responsibilities to user 125 that overlaps with other user(s) 125. Furthermore, network server 160 may assign symmetric and/or asymmetric responsibilities, for example, based on capacity (e.g., availability and skill) of user(s) 125 to perform assigned tasks.

In step 708, network server 160 may determine whether an employee (e.g., user 125) has acknowledged and accepted the task. In some embodiments, network server 160 may automatically determine that user 125 has acknowledged the task if user device 120 associated with a user 125 indicates that the user 125 has accessed or viewed the notification for the task. In some embodiments, network server 160 may determine acknowledgement and acceptance based on an input received from user 125 via user device 120. In some embodiments, network server 160 may determine that acknowledgement acceptance based on one or more sensor devices of a real time locating system. For example, network server 160 may determine user 125 accepted a task based on user 125 being located proximate the task. If no indication of acceptance ("NO"; step 706) is received after a predetermined amount of time (e.g., about 5 minutes), network server 160 may send a reminder notification to the selected user(s) 125 in step 706 to ensure receipt. In some embodiments, if there is no acceptance from selected users 125, network server 160 may alter the determination of the selected user(s) 125 and send notifications to additional user(s) 125 in step 706 to increase chances that the task is completed.

Once a selected user 125 acknowledges receipt of the notification and accepts the task ("YES"; step 708), network server 160 may proceed to step 710 to change the status of the bed to "acknowledged." In some embodiments, network server 160 may transmit an indication to one or more user(s) 125 indicating the acknowledged status of the task. For example, network server 160 may transmit an indication to selected user(s) including supervisors and/or other employees responsible for the task. For instance, network server 160 may generate the indication by generating or updating a GUI including the acknowledged status. The indication may be transmitted to one or more of user interface 120, computer terminal 140, and/or third party server 170. Network server 160 may also determine and indicate subsequent states of the task, such as when user 125 is en route to the task area (e.g., "dispatched") and/or when user is engaged in the task ("in progress"). For example, in some embodiments, network server 160 may determine that user 125 is en route to the task area according to RTLS data, and determine when the user is engaging a discharge assignment according to sensors in the bed. Network server 160 may indicate the progress of the task in a similar manner. Network server 160 may then proceed to step 712.

In step 712, network server 160 may determine whether the employee (e.g., user 125) has indicated that the task is completed. This determination of step 712 may be performed in a similar manner as step 708, requiring an action by user 125 to update network server 160. If user 125 does not indicate that the task is completed ("NO"; step 712), network server 160 may return to step 710. If user 125 indicates that the task is completed ("YES"; step 712), network server 160 may proceed to step 714. In some embodiments, user 125 may alternatively indicate that the task is delayed or suspended. For example, network server 160 may accordingly delay or suspend the task for a predetermined time period or as otherwise indicated.

In step 714, network server 160 may automatically generate an indication to selected employees (e.g., users 125) indicating that the task is completed. For instance, network server 160 may generate the indication by generating or updating a GUI including the status. The indication may be transmitted to one or more of user device 120, computer terminal 140, and/or third party server 170, similar to step 710.

In step 716, network server 160 may record details of task and update data stored in a database. In some embodiments, network server 160 may record the identity of user 125 that received the notifications in step 706 and/or completed the task in steps 708 and/or 712. Network server 160 may also record the type of task, date, time, duration of task, and/or any other details of the performance of the task. The data may be stored in one or more of one or more of database 180, memory 250, memory 340, and database 470.

The foregoing description has been presented for purposes of illustration. It is not exhaustive and is not limited to the precise forms or embodiments disclosed. Modifications and adaptations of the embodiments will be apparent from consideration of the specification and practice of the disclosed embodiments. For example, the described implementations include hardware, firmware, and software, but systems and methods consistent with the present disclosure can be implemented as hardware alone.

Computer programs based on the written description and methods of this specification are within the skill of a software developer. The various programs or program modules can be created using a variety of programming techniques. For example, program sections or program modules can be designed in or by means of Java, C, C++, assembly language, or any such programming languages. One or more of such software sections or modules can be integrated into a computer system, non-transitory computer-readable media, or existing communications software.

Moreover, while illustrative embodiments have been described herein, the scope includes any and all embodiments having equivalent elements, modifications, omissions, combinations (e.g., of aspects across various embodiments), adaptations or alterations based on the present disclosure. Further, the steps of the disclosed methods can be modified in any manner, including by reordering steps or inserting or deleting steps.

The invention claimed is:

1. A computerized system for event monitoring and automating electronic communications, comprising:
   a storage medium storing instructions;
   at least one network interface for bidirectional communication with a plurality of mobile devices on at least one computer network, the plurality of mobile devices comprising employee devices and one or more supervisor devices;
   a real time locating system comprising a plurality of wireless receivers in a facility, patient RFID badges, and occupancy bed weight sensors; and
   at least one processor communicatively connected to the at least one network interface, the real time locating system, and the storage medium, wherein the instructions configure the at least one processor to perform operations comprising:
receiving, via the at least one network interface from the real time locating system, data indicative of a discharge event from at least one of the plurality of wireless receivers of the real time locating system, the discharge event being associated with one or more rooms, the data indicative of a discharge event comprising tracking data indicating a location of patient with respect to a bed assigned to the patient;
the tracking data being identified based upon one or more of the patient RFID badges corresponding to the patient and a location within the facility of a wireless receiver receiving a transmission from the one or more of the patient RFID badges, and the tracking data being identified based upon information received from at least one of the occupancy bed weight sensors of the bed assigned to the patient;
automatically identifying a department associated with the one or more rooms associated with the discharge event;
automatically receiving, from one or more databases connected to the at least one computer network, cleaning protocol information for the identified department, the cleaning protocol comprising a plurality of milestones to be completed and time requirements for each of the plurality of milestones;
accessing patient information associated with the one or more rooms;
determining the patient information comprises a transmittable disease condition;
in response to determining the patient information comprises the transmittable disease condition:
  accessing a look-up table to determine subtasks that reduce a possible spread of the transmittable disease condition; and
  updating the plurality of milestones of the cleaning protocol information by replacing at least one of the plurality of milestones with the subtasks and updating the time requirements for the cleaning protocol information based upon the updated plurality of milestones;
receiving, from the one or more databases, electronic device contact information and assignment information for a plurality of individuals associated with the cleaning protocol information, wherein the assignment information identifies a workload of a given of the plurality of individuals;
automatically generating first instructions for displaying at least one graphical user interface at least one of the employee devices, the at least graphical user interface comprising a first electronic notification comprising information of the discharge event and at least a first milestone of the cleaning protocol information updated with the plurality of milestones and a second electronic notification comprising information of at least a second milestone of the cleaning protocol information updated with the plurality of milestones;
maintaining a functional relationship between milestones of the cleaning protocol information updated with the plurality of milestones, wherein the functional relationship indicates one of the plurality of milestones is dependent on another of the plurality of milestones being completed and, upon detecting a delay in the another of the plurality of milestones, automatically introducing a delay in a commencement of the one of the plurality of milestones;
generating second instructions for displaying a second graphical user interface at the one or more supervisor devices, the second graphical user interface comprising the workload of the plurality of individuals; the second graphical user interface comprising at least one interactive element for remote adjustments to the assignment information of the plurality of individuals; and
transmitting the first instructions to the at least one of the employee devices and the second instructions to the one or more supervisor devices via the at least one computer network.

2. The computerized system of claim 1, wherein:
the look-up table is stored in the one or more databases;
the look-up table describes a plurality of subtasks based on patient and hospital information, each of the plurality of subtasks being associated with a predetermined condition; and
the subtasks comprise one or more of ultraviolet irradiation and curtain removal.

3. The computerized system of claim 1, wherein the operations further comprise:
receiving real-time information for at least one unscheduled task;
generating, based on the received real-time information, an on-demand workload level; and
modifying an assignment of the plurality of milestones based on the generated on-demand workload level.

4. The computerized system of claim 3, wherein:
the received real-time information includes a real-time occupancy level of the identified department; and
the generated on-demand workload is further based on the real-time occupancy level.

5. The computerized system of claim 1, wherein the operations further comprise:
comparing the assignment information and the workload information of the plurality of individuals to identify a first individual capable of completing one or more of the plurality of milestones;
automatically assigning the one or more of the plurality of milestones to the first individual;
determining the assignment information exceeds a predefined department performance level by a predetermined percentage; and
adjusting, responsive to the assignment information exceeding the predetermined department performance level by the predetermined percentage, the assignment of the one or more of the plurality of milestones by adding or subtracting one or more assignments of the first individual.

6. The computerized system of claim 1, wherein:
the plurality of wireless devices comprise Zigbee devices;
the plurality of wireless devices comprise wireless devices in a lobby of the facility; and
the receiving data indicative of the trigger event comprises receiving a signal from at least one of the plurality of wireless devices in the lobby of the facility.

7. The computerized system of claim 6, wherein the continuously monitoring data comprises determining whether a location of one or more of the patient RFID badges corresponds to the lobby of the facility for a predetermined time period.

8. The computerized system of claim 1, wherein the real time locating system further comprises employee RFID badges and equipment RFID tags.

9. The computerized system of claim 1, wherein the first graphical user interface and the second graphical user interface are formatted for a mobile device.

10. The computerized system of claim 1, wherein the transmitting the first instructions to the first device and the second instructions to the second device comprises transmitting one or more push notifications.

11. A computerized method for event monitoring and automating electronic communications, the method comprising:
receiving, via at least one network interface associated with a real time locating system, the real time locating system comprising a plurality of wireless receivers in a facility, patient RFID badges, and occupancy bed weight sensors, data indicative of a discharge event from at least one of the plurality of wireless receivers of the real time locating system, the discharge event being associated with one or more rooms, the data indicative of a discharge event comprising tracking data indicating a location of patient with respect to a bed assigned to the patient;
the tracking data being identified based upon one or more of the patient RFID badges corresponding to the patient and a location within the facility of a wireless receiver receiving a transmission from the one or more of the patient RFID badges, and the tracking data being identified based upon information received from at least one of the occupancy bed weight sensors of the bed assigned to the patient;
automatically identifying a department associated with the one or more rooms associated with the discharge event;
automatically receiving, from one or more databases connected to the at least one computer network, cleaning protocol information for the identified department, the cleaning protocol comprising a plurality of milestones to be completed and time requirements for each of the plurality of milestones;
accessing patient information associated with the one or more rooms;
determining the patient information comprises a transmittable disease condition;
in response to determining the patient information comprises the transmittable disease condition:
  accessing a look-up table to determine subtasks that reduce a possible spread the transmittable disease condition; and
  updating the plurality of milestones of the cleaning protocol information by replacing at least one of the plurality of milestones with the subtasks and updating the time requirements for the cleaning protocol information based upon the updated plurality of milestones;
receiving, from the one or more databases, electronic device contact information and assignment information for a plurality of individuals associated with the cleaning protocol information, wherein the assignment information identifies a workload of a given of the plurality of individuals;
automatically generating first instructions for displaying at least one graphical user interface at least one of the employee devices, the at least graphical user interface comprising a first electronic notification comprising information of the discharge event and at least a first milestone of the cleaning protocol information updated with the plurality of milestones and a second electronic notification comprising information of at least a second milestone of the cleaning protocol information updated with the plurality of milestones;
maintaining a functional relationship between milestones of the cleaning protocol information updated with the plurality of milestones, wherein the functional relationship indicates one of the plurality of milestones is dependent on another of the plurality of milestones being completed and, upon detecting a delay in the another of the plurality of milestones, automatically introducing a delay in a commencement of the one of the plurality of milestones;
generating second instructions for displaying a second graphical user interface at the one or more supervisor devices, the second graphical user interface comprising the workload of the plurality of individuals; the second graphical user interface comprising at least one interactive element for remote adjustments to the assignment information of the plurality of individuals; and
transmitting the first instructions to the at least one of the employee devices and the second instructions to the one or more supervisor devices via the at least one computer network.

12. The computerized method of claim 11, wherein:
the look-up table is stored in the one or more databases;
the look-up table describes a plurality of subtasks based on patient and hospital information, each of the plurality of subtasks being associated with a predetermined condition; and
the subtasks comprise one or more of ultraviolet irradiation and curtain removal.

13. The computerized method of claim 11, further comprising:
receiving real-time information for at least one unscheduled task;
generating, based on the received real-time information, an on-demand workload level; and
modifying an assignment of the plurality of milestones based on the generated on-demand workload level.

14. The computerized method of claim 13, wherein:
the received real-time information includes a real-time occupancy level of the identified department; and
the generated on-demand workload is further based on the real-time occupancy level.

15. The computerized method of claim 11, further comprising:
comparing the assignment information and the workload information of the plurality of individuals to identify a first individual capable of completing one or more plurality of milestones;
automatically assigning the one or more plurality of milestones to the first individual;
determining the assignment information exceeds a predefined department performance level by a predetermined percentage; and
adjusting, responsive to the assignment information exceeding the predetermined department performance level by the predetermined percentage, the assignment of the one or more plurality of milestones by adding or subtracting one or more assignments of the first individual.

16. A non-transitory computer readable medium storing instructions which, when executed, cause at least one networked processor to perform operations for event monitoring and automating electronic communications, the operations comprising:
receiving, via at least one network interface associated with a real time locating system, the real time locating system comprising a plurality of wireless receivers in a facility, patient RFID badges, and occupancy bed weight sensors, data indicative of a discharge event from at least one of the plurality of wireless receivers of the real time locating system, the discharge event being associated with one or more rooms, the data indicative of a discharge event comprising tracking data indicating a location of patient with respect to a bed assigned to the patient;

the tracking data being identified based upon one or more of the patient RFID badges corresponding to the patient and a location within the facility of a wireless receiver receiving a transmission from the one or more of the patient RFID badges, and the tracking data being identified based upon information received from at least one of the occupancy bed weight sensors of the bed assigned to the patient;

automatically identifying a department associated with the one or more rooms associated with the discharge event;

automatically receiving, from one or more databases connected to the at least one computer network, cleaning protocol information for the identified department, the cleaning protocol comprising a plurality of milestones to be completed and time requirements for each of the plurality of milestones;

accessing patient information associated with the one or more rooms;

determining the patient information comprises a transmittable disease condition;

in response to determining the patient information comprises the transmittable disease condition:
  accessing a look-up table to determine subtasks that reduce a possible spread the transmittable disease condition; and
  updating the plurality of milestones of the cleaning protocol information by replacing at least one of the plurality of milestones with the subtasks and updating the time requirements for the cleaning protocol information based upon the updated plurality of milestones;

receiving, from the one or more databases, electronic device contact information and assignment information for a plurality of individuals associated with the cleaning protocol information, wherein the assignment information identifies a workload of a given of the plurality of individuals;

automatically generating first instructions for displaying at least one graphical user interface at least one of the employee devices, the at least graphical user interface comprising a first electronic notification comprising information of the discharge event and at least a first milestone of the cleaning protocol information updated with the plurality of milestones and a second electronic notification comprising information of at least a second milestone of the cleaning protocol information updated with the plurality of milestones;

maintaining a functional relationship between milestones of the cleaning protocol information updated with the plurality of milestones, wherein the functional relationship indicates one of the plurality of milestones is dependent on another of the plurality of milestones being completed and, upon detecting a delay in the another of the plurality of milestones, automatically introducing a delay in a commencement of the one of the plurality of milestones;

generating second instructions for displaying a second graphical user interface at the one or more supervisor devices, the second graphical user interface comprising the workload of the plurality of individuals; the second graphical user interface comprising at least one interactive element for remote adjustments to the assignment information of the plurality of individuals; and transmitting the first instructions to the at least one of the employee devices and the second instructions to the one or more supervisor devices via the at least one computer network.

17. The non-transitory computer readable medium of claim 16, wherein:
  the look-up table is stored in the one or more databases;
  the look-up table describes a plurality of subtasks based on patient and hospital information, each of the plurality of subtasks being associated with a predetermined condition; and
  the subtasks comprise one or more of ultraviolet irradiation and curtain removal.

18. The non-transitory computer readable medium of claim 16, wherein the operations further comprise:
  receiving real-time information for at least one unscheduled task;
  generating, based on the received real-time information, an on-demand workload level; and
  modifying an assignment of the plurality of milestones based on the generated on-demand workload level.

19. The non-transitory computer readable medium of claim 18, wherein:
  the received real-time information includes a real-time occupancy level of the identified department; and
  the generated on-demand workload is further based on the real-time occupancy level.

20. The non-transitory computer readable medium of claim 16, the operations further comprising:
  comparing the assignment information and the workload information of the plurality of individuals to identify a first individual capable of completing one or more plurality of milestones;
  automatically assigning the one or more plurality of milestones to the first individual;
  determining the assignment information exceeds a predefined department performance level by a predetermined percentage; and
  adjusting, responsive to the assignment information exceeding the predetermined department performance level by the predetermined percentage, the assignment of the one or more plurality of milestones by adding or subtracting one or more assignments of the first individual.

* * * * *